United States Patent
Murso et al.

(10) Patent No.: US 9,688,632 B2
(45) Date of Patent: Jun. 27, 2017

(54) METHOD FOR MANUFACTURING MAGNESIUM AMIDES

(76) Inventors: Alexander Murso, Frankfurt (DE); Christopher Kurth, Münster (DE); Peter Rittmeyer, Sulzbach/Taunus (DE)

( * ) Notice: Subject to any disclaimer, the term of this patent is extended or adjusted under 35 U.S.C. 154(b) by 198 days.

(21) Appl. No.: 12/990,866

(22) PCT Filed: May 18, 2009

(86) PCT No.: PCT/EP2009/055987
§ 371 (c)(1),
(2), (4) Date: Nov. 3, 2010

(87) PCT Pub. No.: WO2009/141300
PCT Pub. Date: Nov. 26, 2009

(65) Prior Publication Data
US 2011/0060144 A1 Mar. 10, 2011

(30) Foreign Application Priority Data
May 21, 2008 (DE) .......... 10 2008 001 905

(51) Int. Cl.
*C07D 211/12* (2006.01)
*C07F 3/00* (2006.01)

(52) U.S. Cl.
CPC ............ *C07D 211/12* (2013.01); *C07F 3/003* (2013.01)

(58) Field of Classification Search
USPC ....... 546/184; 556/412; 564/209, 463; 568/9
See application file for complete search history.

(56) References Cited

U.S. PATENT DOCUMENTS

| | | | | |
|---|---|---|---|---|
| 3,758,620 | A * | 9/1973 | Vit .............................. | 260/665 G |
| 5,320,744 | A * | 6/1994 | Steffens ................. | B01J 8/0055 208/113 |
| 5,320,774 | A * | 6/1994 | Mehta et al. ............ | 252/182.12 |
| 5,952,537 | A | 9/1999 | Stickley et al. | |
| 6,303,057 | B1 | 10/2001 | Stickley et al. | |
| 6,515,141 | B1 | 2/2003 | Goto et al. | |
| 7,250,535 | B2 * | 7/2007 | Maehara ............... | C07F 9/5068 568/9 |
| 8,134,005 | B2 * | 3/2012 | Knochel ................ | C07B 49/00 546/184 |
| 2009/0176988 | A1 | 7/2009 | Knochel et al. | |

FOREIGN PATENT DOCUMENTS

| | | |
|---|---|---|
| EP | 1 207 153 A | 5/2002 |
| EP | 1 810 974 A1 | 7/2007 |
| WO | WO 99/46224 A | 9/1999 |
| WO | WO2007082911 * | 7/2007 |

OTHER PUBLICATIONS

"Preparation of Grignard" Wikipedia p. 1-13 (2014).*
Hieme "Chemistry" p. 840-841 (2002).*
WebElement p. 1 internet (2015).*
Alverez et al. "Unmasking representative . . . " Agnewandte v.47, p. 8079-8081 (2008).*
Krasovskiy et al. Angew. Chem. Int. 45 p. 2958-2961 (2006).*
Ren et al. "Stereoselective . . . " Am. Chem. Soc. Org, Lett. v.6, p. 4215-4217 (2004).*
Wikipedia "Grignard reation" p. 1-9 (2012).*
Norman et al. "Principle of org . . . " p. 187-188 (1993).*
Rappoport et al. "The chemistyr . . . R-Mg" p. 414, 421-424 (2008).*
Thieme "Chemistry" p. 840-841 (2002).*
"One pot" synthesis, Wikipdia p. 1 (2014).*
Piller, FM "Thesis" p. 1-187 (2010).*
Clososki, et al. "Direct magnesization of functionalized arenes and heteroarenes with $(tmp)_2Mg$ $2LiCl$", *Angew. Chem.* 119 (2007), pp. 7825-7828, with English translation.
Krasovskiy, et al. "Mixed Mg/Li amides of type $R_2NMgCl$ LiCl as highly efficient bases for the regioselective synthesis of functionalized aryl and heteroaryl magnesium compounds", *Angew, Chem.* 118 (2006), pp. 3024-3027, with English translation.
"Methods of Organic Chemistry", editor Eugen Mueller, Georg Thieme Velag Stuttgart, vol. XIII/2a (1973), pp. 279-280, with English translation.
Eaton, et al. "Transmetalation and Reverse Transmetalation on Ortho-Activated Aromatic Compounds: A Direct Route to o , o'-Disubstrituted Benzenes", *J.Org.Chem.* 53 (1988), pp. 2728-2732.
Frostick, et al. "Condensations of Esters by Diisopropylaminomagnesium Bromide and Certain Related Reagents", *J. Am. Chem. Soc.* (1949), 71, pp. 1350-1352.

* cited by examiner

*Primary Examiner* — Celia Chang

(57) ABSTRACT

A method for manufacturing amidomagnesium halogenides and admixtures thereof with alkali metal salts in aparotic, organic solvents, compounds obtained according to the method and use thereof in synthesis chemistry, for example for deprotonizing enolizable systems, functionalized aromatics and heteroaromatics.

15 Claims, No Drawings

METHOD FOR MANUFACTURING MAGNESIUM AMIDES

RELATED APPLICATIONS

This application is a §371 application of PCT/EP2009/055987 filed May 18, 2009, which claims priority from German Patent Application No. 10 2008 001 905.4 filed May 21, 2008.

The present invention relates to a method for producing amidomagnesium halogenides, and also to the admixture thereof with alkali-metal salts in aprotic, organic solvents, to the compounds that can be obtained according to this method, and to the application thereof in synthesis chemistry, for example for the deprotonization of enolizable systems, functionalized aromatics and heteroaromatics.

Magnesium amides of the general form (R'R"NMgX) and also the admixture thereof with alkali-metal salts of the form M have wide-spread application in synthesis chemistry. Compared with lithium amides or organolithium compounds they exhibit lower nucleophilicity, as a result of which higher levels of selectivity and yields are achieved. They are often employed in deprotonization reactions on enolizable systems or on functionalized aromatics and heteroaromatics. In the presence of alkali-metal salts, for example LiCl, they exhibit an increased kinetic basicity, as a result of which reaction times are significantly shortened. The use of amidomagnesium halogenides permits, moreover, syntheses under non-cryogenic conditions. Moreover, on account of other regioselectivities in comparison with similar reagents, such as, for example, lithium amides, they permit the production of intermediates that cannot be obtained in another way or can only be obtained by way of a plurality of synthesis steps (A. Krasovskiy, V. Krasovskaya, P. Knochel, Angew. Chem, 2006, 118, 3024; b) W. Lin, O. Baron, P. Knochel, Org. Lett. 2006, 8, 5673; c) G. C. Clososki, C. J. Rohbogner, P. Knochel, Angew. Chem. 2007, 119, 7825; d) P. E. Eaton, B. M, Martin, J. Org. Chem. 1988, 53, 2728, e) Y. Kondo, A. Yoshida, T. Sakamoto, J. Chem. Soc. Perkin Trans. 1, 1996, 2331 and literature cited therein and EP 1810974 A1).

Amidomagnesium halogenides (R'R"NMgX) are generally obtained by causing Grignard reagents ($R^1$MgX) to react with the corresponding amines (R'R"NH). The amines (R'R"NH) react in this case with the Grignard compound ($R^1$MgX) in the first instance with the formation of an electron-donor-acceptor complex which then with the elimination of $R^1$—H is converted to form the amidomagnesium halogenide (R'R"NMgX) (Methoden der Organischen Chemie (Houben-Weyl), E. Müller (Eds.), Vol. XIII/2a, 4th edition, published by Thieme Verlag, Stuttgart, 1973 and literature cited therein and F. C. Frostick Jr., C. R. Hauser, J. Am. Chem. Soc. 1949, 71, 1350).

Mixtures of amidomagnesium halogenides (R'R"NMgX) with alkali-metal salts MY can be obtained by means of the reaction of Grignard compounds with amines and the later addition of the alkali-metal salt or by the addition of the alkali-metal salt to the Grignard compound and the subsequent reaction with an amine (Figure 1).

Figure 1: Production of amidomagnesium halogenides
(R'R"NMgX) and the admixtures thereof with alkali-metal salts (MY).

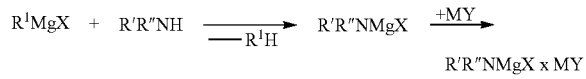

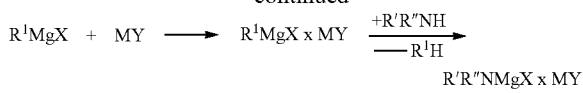

The latter way is described, for example, by Knochel et al. In EP 1810974 A1 there is a report on the production and use of, for example, TMPMgCl/LiCl, ca. 1M in THF (TMP=2,2,6,6-tetramethylpiperidino). The production is effected by causing the reaction of turbo-Grignard reagents, for example iso-PrMgCl/LiCl, ca. 14% in THF, and TMPH (2,2,6,6-tetramethylpiperidine) in accordance with Figure 2.

Figure 2: Production of TMPMgCl/LiCl in THF

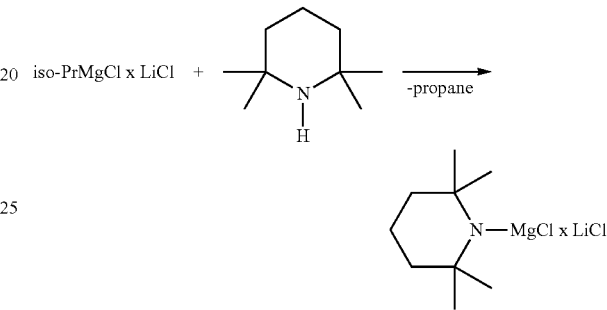

All previously known ways for producing amidomagnesium halogenides (R'R"NMgX) and also the admixtures thereof with alkali-metal salts require in a first step always the production of a suitable Grignard compound ($R^1$MgX) or the mixture thereof with alkali-metal salt followed by a reaction of the Grignard compound that is gained with a corresponding amine and, if applicable, later introduction of the alkali-metal salt. The known methods for producing amidomagnesium halogenides (R'R"NMgX) or the mixtures thereof with alkali-metal salts (MY) thus represent at least two-step, expensive and technically demanding processes.

An object of the present invention is therefore to provide a method that overcomes the disadvantages of the prior art. In particular, the present invention was based on developing a simple, single-step and economical method for producing amidomagnesium halogenides (R'R"NMgX) and also the admixture thereof with alkali-metal salts (MY).

In accordance with the invention, surprisingly the object is achieved as follows.

The method in accordance with the invention delivers a plurality of amidomagnesium halogenides (R'R"NMgX). The method in accordance with the invention delivers similarly or differently substituted amidomagnesium halogenides (R'R"NMgX) in just one defined solvent or in defined solvent mixes. In addition, the method in accordance with the invention delivers alkali-salt-containing or alkali-salt-free solutions of amidomagnesium halogenides (R'R"NMgX) in defined solvents or solvent mixes. The amidomagnesium halogenides (R'R"NMgX) produced in accordance with the invention and also the mixtures thereof with alkali-metal salts MY can be used to produce numerous in part highly functionalized substances, such as pharmaceuticals, natural-substance derivatives, polymer materials, agricultural chemicals, specialities and catalysts, for example in deprotonization reactions and for the production of zinc amides.

Surprisingly it has been found that by reacting magnesium with an organic halogenide (R'X) in an aprotic organic solvent in the presence of a protic amine (R'R"NH) the desired amidomagnesium halogenides (R'R"NMgX) are formed directly in high yields and with high purity. In order to produce mixtures of amidomagnesium halogenides (R'R"MgX) and alkali-metal salts (MY) the reaction is preferably carried out directly in the presence of the alkali-metal salt. It is, however, also possible to introduce the alkali-metal salt (MY) only once the reaction is complete.

The formation of the desired amidomagnesium halogenides (R'R"NMgX) shows that during the reaction a Grignard compound (R'MgX) develops that is then captured directly by the protic amine (R'R"NH), as a result of which the desired amidomagnesium halogenides (R'R"NMgX) are formed with the elimination of $R^1$—H.

The competing reaction of the amine with magnesium would result in the formation of hydrogen ($H_2$) and a magnesium amide of the form (R'R"N)$_2$Mg. However, this is not observed in the method in accordance with the invention.

The formation of amidomagnesium halogenides (R'R"NMgX) according to the method in accordance with the invention is contrary to the expectation that in the presence of protic compounds, such as, for example, water, alcohols or amines, the formation of Grignard compounds ($R^1$MgX) is hindered to a very great extent, something which results in the Grignard formation not being initiated at all or only after the addition of considerable quantities of halogenide ($R^1$X). Thus, for example, it is specified that in order to produce Grignard compounds all the reagents and apparatus used must be dry and ideally should contain less than 0.02% by weight water (Handbook of Grignard Reagents, G. S. Silverman, P. E. Rakita (Eds.), Marcel Dekker, Inc., New York, 1996). If the Grignard formation is only initiated after the addition of considerable quantities of organic halogenide ($R^1$X), increasingly a Wurtz coupling occurs as a side reaction as a result of reaction of the accumulated organic halogenide (Eft) with Grignard reagent ($R^1$MgX) formed, something which results in the formation of considerable quantities of undesirable by-product ($R^1$-$R^1$).

The use of tertiary amines ($R_3$N) as a solvent is known in the production and application of Grignard compounds. These form electron-donor-acceptor complexes with Grignard reagents. If at the same time other donor solvents, for example etheric solvents, are used in the Grignard production or the application of Grignard compounds, tertiary amines can displace the etheric solvent, depending on the donor strength. They thus influence the aggregation, solubility and also the reactivity of Grignard compounds.

The invention is explained with the aid of the following general Figure 3,

Figure 1: Production in accordance with the invention of amidomagnesium halogenides (R'R"NMgX) and the admixture thereof with alkali-metal salts (MY).

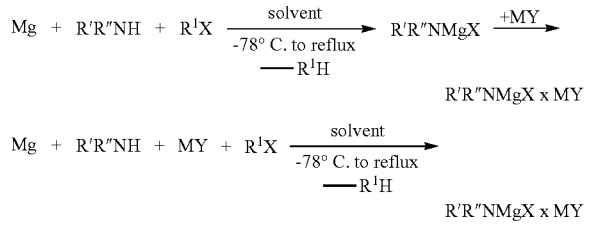

The method in accordance with the invention is generally carried out as follows:

Magnesium is placed in an aprotic organic solvent or solvent mix and a protic amine (R'R"NH), and is induced to react with a halogenide ($R^1$X).

Preferably, magnesium is placed in an aprotic organic solvent or solvent mix and an amine R (R'R"NH), and an organic halogenide ($R^1$X) is metered into this mixture.

In a further embodiment, magnesium is placed in an aprotic organic solvent or solvent mix, and a protic amine (R'R"NH) and an organic halogenide ($R^1$X) are metered in as a mixture or individually in parallel.

In order to produce mixtures of R'R"NMgX with alkali salts (MY), the alkali-metal salt is preferably also placed therewith.

The quantity of alkali-metal salt that is dissolved in the product solution is thereby determined by the molar ratio of alkali salt (MY) to product R'R"NMgX that is striven for, the concentration of product R'R"NMgX and the solvent or solvent mix. The solubility of the alkali-metal salt and thus also the molar ratio of MY to R'R"NMgX falls with increasing product concentration. Likewise, the solubility of alkali salt falls with increasing content of non-polar solvents.

The production concentration of R'R"NMgX, amounts to between 5 and 80% by weight, preferably to between 5 and 50% by weight.

Preferably an excess of 0-50%, by preference between 0-20%, particularly preferably between 0-10%, alkali salt is employed in relation to the desired molar ratio of MY to R'R"NMgX.

If molar ratios of MY to R'R"NMgX≥1 are striven for, the excess of alkali salt (MY) to organic halogenide ($R^1$X) amounts to between 0-50%, preferably to between 0-20%.

Mg blocks, chips, raspings, granules or even Mg powder can be used as the magnesium; preferably Mg chips, raspings, granules or powder are used as the magnesium.

The magnesium can be activated with methods of the prior art before the start of the reaction in order to minimize side 1.5 reactions, such as, for example, the Wurtz reaction, for example by adding iodine, 1,2-dibromomethane, trimethylsilyl chloride, previously produced Grignard solution ($R^1$MgX) or previously produced product R'R"NMgX or the admixtures thereof with an alkali salt (MY). Preferably there is activation with previously produced Grignard solution (R'MgX) or previously produced product R'R"NMgX or the admixtures thereof with an alkali salt (MY). The quantity of Grignard solution (R'MgX) or previously produced product R'R"NMgX or the admixtures thereof with an alkali salt (MY) for the purposes of activation amounts to between 0.01 and 50 mol % relative to the quantity of magnesium presented and preferably to between 0.1 and 10 mol %.

The methods are carried out between −78° C. and reflux temperature of the reaction suspension, preferably between 0° C. and reflux temperature.

The excess of magnesium in relation to the organic halogenide ($R^1$X) amounts to between 0 and 300%, preferably to between 10 and 200%.

The molar ratio of protic amine (R'R"NH) to organic halogenide ($R^1$X) amounts to between 0.7 and 1.5, preferably to between 0.9 and 1.3, particularly preferably to between 1.0 and 1.2.

In order to produce R'R"NMgX solutions and also the mixtures thereof with alkali salt (MY) in mixtures of ethers and hydrocarbons, preferably organic halogenides ($R^1$X) are used that produce the desired hydrocarbon during the reaction, for example pentyl chloride or bromide, hexyl chloride or bromide or the isomers thereof, cyclohexyl chloride or bromide, phenyl chloride or bromide or benzyl chloride or bromide.

In order to produce R'R"NMgX solutions or mixtures with alkali salt (MY) in pure ethers, preferably organic halogenides ($R^1X$) are used that form volatile gases during the reaction, for example methyl chloride or bromide, ethyl chloride or bromide, n- or iso-propyl chloride or bromide or n-, sec- or tent-butyl chloride or bromide.

Common methods of the prior art are used in order to process the reaction mixture; preferably there is filtering by way of a suitable filter or siphoning-off after settling of the solid matter that is still present.

If there is siphoning-off, preferably a residue of reaction mixture remains in the reactor. This residue can also be used in follow-up preparations. It contains active magnesium, so no further activation of the magnesium is required for follow-up preparations.

Alkali-metal salts for the purposes of the invention are compounds of the general formula MY,
wherein M is lithium, sodium and potassium, preferably lithium and potassium, particularly preferably lithium, and wherein Y is selected from chloride, bromide, iodide or OZ,
wherein OZ represents an alcoholate anion, and Z is chosen from an organic, branched or unbranched, saturated or unsaturated, aliphatic or aromatic carbon fragment that contains between one and 20 carbon atoms or is chosen from $R^2R^3R^4Si$, where $R^2$, $R^3$ and $R^4$ are as defined below,
wherein fragments with one to 10 carbon atoms and $R^2R^3R^4Si$ are preferred,
wherein methyl, ethyl, n-propyl, iso-propyl, n-butyl, sec-butyl, tert-butyl, tert-amyl, phenyl and $R^2R^3R^4Si$ are particularly preferred.

In particular, as regards MY, lithium chloride, lithium bromide, lithium methoxide, lithium ethoxide, lithium-n-propoxide, lithium-iso-propoxide, lithium-tert-butoxide, lithium-tert-amoxide, lithium-trimethylsilyl oxide, lithium-tri-tert-butylsilyl oxide are preferably used.

In the organic halogenides ($R^1X$), the Grignard compounds (R'MgX) and the products R'R"NMgX, X is chosen from chlorine, bromine or iodine, preferably from chlorine and bromine; chlorine is particularly preferred.

In the organic halogenides ($R^1X$), the protic amines (R'R"NH), the Grignard compounds ($R^1MgX$) and the silyl fragments ($R^2R^3R^4Si$), $R^1$, $R^2$, $R^3$, $R^4$, R' and R" are chosen independently of one another from:
saturated, unsaturated, branched, unbranched, functionalized, unfunctionalized, aliphatic, cyclic, heterocyclic or aromatic organic fragments, wherein
saturated, unsaturated, branched, unbranched, functionalized, unfunctionalized, aliphatic, cyclic, heterocyclic or aromatic organic fragments with 1 to 20 carbon atoms are preferred, wherein
in particular methyl, ethyl, n-propyl, iso-propyl, n-butyl, sec-butyl, tert-butyl, pentyl-, hexyl-, heptyl-, octyl-, cyclohexyl, phenyl and benzyl fragments are particularly preferred, and wherein
as regards organic halogenides ($R^1X$) what are preferred in particular are methyl chloride or bromide, ethyl chloride or bromide, n- or iso-propyl chloride or bromide, n-, sec- or tert-butyl chloride or bromide, n-, iso-, sec- or tert-pentyl chloride or bromide, n-hexyl chloride or bromide, chlorobenzene or bromobenzene or benzyl chloride or bromide, and wherein
as regards protic amines (R'R"NH) what are preferred in particular are dimethylamine, diethylamine, di-n-propylamine, di-iso-propylamine (DIPA), di-n-butylamine, di-sec-butylamine, di-tert-butylamine, dicyclohexylamine, N-tert-butyl-iso-propylamine, hexamethyldisilazane, piperidine and 2,2,6,6,-tetramethylpiperidine (TMP).

As aprotic, organic solvents, aliphatic or aromatic hydrocarbons, heterocycles, ethers or mixtures thereof are preferred; ethers or mixtures of ethers and aliphatic or aromatic hydrocarbons are particularly preferred; ethers are especially preferred.

Cyclic, saturated, unsaturated, branched and unbranched hydrocarbons come under the term aliphatic hydrocarbons.

Saturated or cyclic, branched or unbranched hydrocarbons with 5 to 20 hydrocarbons are preferably used; n-pentane, n-hexane, n-heptane, n-octane or the isomers thereof, cyclopentane, cyclohexane and methylcyclohexane are particularly preferred.

Acyclic, cyclic, saturated, unsaturated, branched, unbranched, similarly substituted and differently substituted ethers with at least one oxygen atom, preferably with one to four oxygen atoms, come under the term ethers. Furthermore, dimethyl ether, diethyl ether, dibutyl ether, dimethoxyethane, diethoxymethane, polyethylene glycol, methyl-tert-butyl ether, cyclopentyl methyl ether, dioxane, tetrahydrofuran (TI-IF) and 2-methyl-tetrahydrofuran (2-methyl-THF) are preferred as ethers, and THF and 2-methyl-THF and cyclopentyl methyl ether are particularly preferred.

Unsubstituted, singly substituted and multiply substituted aromatic compounds come under the term aromatic hydrocarbons. Benzene, toluene, ethyl benzene, cumene and xylene and also their isomers are preferably used.

The Subject Matter of the Invention in Detail is:
a method for producing amidomagnesium halogenides (R'R"NMgX) in aprotic, organic solvents, characterised in that aprotic organic solvents, magnesium, protic amines (R'R"NH) and organic halogenides ($R^1X$) are used for the production;
a method for producing mixtures of amidomagnesium halogenides (R'R"NMgX) with alkali metal salts (MY) in aprotic, organic solvents, characterised in that in addition alkali-metal salts (MY) are also used;
the compounds that are produced according to the method in accordance with the invention;
the use of the compounds that are produced according to the method in accordance with the invention in synthesis chemistry;
the use of the compounds that are produced according to the method in accordance with the invention for the deprotonization of enolizable systems;
the use of the compounds that are produced according to the method in accordance with the invention for the deprotonization of functionalized aromatics and heteroaromatics.

EXAMPLES

The invention is explained with the aid of the following examples without being limited to them. Specialists trained in the field of chemistry will recognize that these examples also point to other procedures that are not specified here in order to obtain the amidomagnesium halogenides (R'R"NMgX) that are produced in accordance with the invention and the admixture thereof with alkali-metal salts (MY).

Many variations and modifications are therefore possible that constitute subject matter of the present invention.

All the experiments were carried out in an argon atmosphere with the use of Schlenk techniques. Technical raw materials were employed. As regards magnesium, Mg-raspings were employed, although in accordance with the invention other grades of magnesium that are suitable for Grignard production can also be used.

In order to illustrate the efficiency of the method, the production of TMPMgCl/LiCl in THF and in THF/toluene, of TMPMgCl in THF/toluene and also of DIPAMgCl/LiCl in THF/toluene was chosen. In order to produce TI-IF solutions iso-propyl chloride was used as the organic halogenide ($R^1X$); in order to produce THF/toluene solutions benzyl chloride was used. It is known that organic bromides ($R^1Br$) are generally better suited for Grignard production than the corresponding chlorides ($R^1Cl$). Thus the choice made underlines the generality of the method. LiCl was chosen as the alkali metal salt, although other alkali-metal salts that are soluble in the medium can also be used.

The examples are explained in the following. The precise quantities of the preparation, excesses, reaction and metering times and also reaction and metering temperatures are specified in Tables 1, 3 and 5. The results of analysis and evaluation of the experiments, including the yields, are specified in Tables 2, 4 and 6.

The precise content and the composition of the charges were determined analytically. The content of magnesium was determined complexometrically, the content of lithium by flame-emission spectroscopy, the content of chloride argentometrically, the content of total base acidimetrically and the amine content according to Kjeldahl after hydrolysis. The active base was determined according to Watson-Eastham.

The identity and purity of the isolated products was confirmed by GC/MS investigations after derivatization and $^1H$- and $^{13}C$-NMR measurements.

Example 1: Production of TMPMgCl/LiCl in THF/Toluene from Mg, LiCl, TMPH and Benzyl Chloride with Activation of the Magnesium with TMPMgCl/LiCl in THF/Toluene Magnesium, THF, lithium chloride, TMPMgCl/LiCl in THF/toluene are suspended in a double-jacket reactor with stirrer, metering station and reflux condenser and stirred for 30 minutes at room temperature. Subsequently, the total quantity of TMPH is added quickly in one portion. Then approximately 5 mol % of the total quantity of benzyl chloride were added quickly. The initiation of the reaction could be established by an immediate noticeable rise in temperature. The residual quantity of benzyl chloride was metered continuously. After a secondary reaction, the solution was filtered. A brownish, clear solution was obtained.

Example 2: Production of TMPMgCl in THF/Toluene from Mg, TMPH and Benzyl Chloride with Activation of the Magnesium with TMPMgCl in THF/Toluene Magnesium, THF, TMPMgCl in THF/toluene are suspended in a double-jacket reactor with stirrer, metering station and reflux condenser and stirred for 30 minutes at room temperature. Subsequently, the total quantity of TMPH was added quickly in one portion. Then approximately 5 mol % of the total quantity of benzyl chloride were added quickly. The initiation of the reaction could be established by an immediate noticeable rise in temperature. The residual quantity of benzyl chloride was metered continuously. After a secondary reaction, the solution was filtered. A brownish, clear solution was obtained.

Example 3: Production of TMPMgCl/LiCl in THF from Mg, LiCl, TMPH and iso-PrCl with Activation of the Magnesium with Iso-PrMgCl in THF Magnesium, THF, lithium chloride and iso-PrMgCl in THF are suspended in a double-jacket reactor with stirrer, metering station and reflux condenser and stirred for 30 minutes at room temperature. The total quantity of TMPH was added quickly in one portion. The quantity that is required for the reaction of iso-PrMgCl with TMPH to give the desired product according to Figure 1 is taken into consideration in the total quantity of TMPH. Approximately 5 mol % of the total quantity of iso-PrCl were added quickly. The initiation of the reaction could be established by an immediate noticeable rise in temperature. The residual quantity of iso-PrCl was metered continuously. After a secondary reaction, the solution was filtered. A brownish, clear solution was obtained.

Example 4: Production of DIPAMgCl/LiCl in THF/Toluene from Mg, LiCl, DIPAH and Benzyl Chloride without Activation of the Magnesium Magnesium, THF, lithium chloride and the total quantity of DIPAH are placed in a double-jacket reactor with stirrer, metering station and reflux condenser. Approximately 5 mol % of the total quantity of benzyl chloride were added quickly. The initiation of the reaction could be established by an immediate noticeable rise in temperature. The residual quantity of benzyl chloride was metered continuously. After a secondary reaction, the solution was filtered. A brownish, clear solution was obtained.

TABLE 1

Production parameters for TMPMgCl/LiCl in THF/toluene and TMPMgCl in THF/toluene

| | TMPH | | BC[1] | | Mg | | LiCl | | | Mg-activation | | Temp. | Metering time | Secondary reaction |
|---|---|---|---|---|---|---|---|---|---|---|---|---|---|---|
| Example | g | mmol | g | mmol | g | mmol | g | mmol | THF g | mmol | substance | °C. | min | min °C. |
| 1 | 85.91 | 608.17 | 67.22 | 531.01 | 26.8 | 1102.4 | 29.45 | 694.74 | 287.8 | 20.90 | TMPMgCl[2] | 25 | 240 | 120  25 |
| 2 | 78.00 | 552.17 | 66.95 | 528.87 | 24.9 | 1024.3 | — | — | 515.2 | 21.50 | TMPMgCl[3] | 25 | 300 | 120  25 |

[1]BC = benzyl chloride;
[2]TMPMgCl/LiCl in THF/toluene: active base AB = 0.96 mmol/g;
[3]TMPMgCl in THF/toluene: active base AB = 0.66 mmol/g.

TABLE 2

Results for the Examples from Table 1

| Example | OH | Mg | Cl | Li | TMPH | AB[1] | LiCl[2] | Ratio LiCl:AB | Yield[3] % AB[4] | % LiCl[5] | % TMPH[5] | Concentration Weight % |
|---|---|---|---|---|---|---|---|---|---|---|---|---|
| | mmol/g | | | | | | mmol/g | | | | | |
| 1 | 2.30 | 1.10 | 2.18 | 1.03 | 1.23 | 1.05 | 1.03 | 0.98 | 91.3 | 68.5 | 93.4 | 21.0 |
| 2 | 1.50 | 0.75 | 0.77 | — | 0.77 | 0.71 | — | — | 88.6 | — | 92.1 | 13.8 |

[1]AB = active base;
[2]over Li;
[3]isolated yield without wash solutions;
[4]relative to quantity of benzyl chloride BC;
[5]relative to quantity used.

TABLE 3

Production parameters for TMPMgCl/LiCl in THF

| Example | TMPH g | mmol | iso-PrCl g | mmol | Mg g | mmol | LiCl g | mmol | THF g | Mg-activation mmol substance | Temp. ° C. | Metering time min | Secondary reaction min | ° C. |
|---|---|---|---|---|---|---|---|---|---|---|---|---|---|---|
| 3 | 89.30 | 632.17 | 44.80 | 570.41 | 16.0 | 659.8 | 25.34 | 597.78 | 340.7 | 56.80 iso-PrMgCl[1] | 45 | 200 | 90 | 45 |

[1]iso-PrMgCl in THF: active base AB = 1.33 mmol/g.

TABLE 4

Results for the Examples from Table 3

| Example | OH | Mg | Cl | Li | TMPH | AB[1] | LiCl[2] | Ratio LiCl:AB | Yield[3] % AB[4] | % LiCl[5] | % TMPH[5] | Concentration Weight % |
|---|---|---|---|---|---|---|---|---|---|---|---|---|
| | mmol/g | | | | | | mmol/g | | | | | |
| 3 | 2.33 | 1.08 | 2.19 | 1.11 | 1.23 | 1.07 | 1.11 | 1.04 | 92.4 | 91.4 | 95.8 | 21.4 |

[1]AB = active base;
[2]over Li;
[3]isolated yield without wash solutions;
[4]relative to quantity of iso-PrCl;
[5]relative to quantity used.

TABLE 5

Production parameters for DIPAMgCl/LiCl in THF/toluene

| Example | DIPAH[1] g | mmol | BC[2] g | mmol | Mg g | mmol | LiCl g | mmol | THF g | Mg-activation mmol substance | Temp. ° C. | Metering time min | Secondary reaction min | ° C. |
|---|---|---|---|---|---|---|---|---|---|---|---|---|---|---|
| 4 | 69.27 | 684.55 | 82.67 | 653.05 | 33.5 | 1375.98 | 30.10 | 710.07 | 772.9 | — — | 25-35 | 260 | 25 | 100 |

[1]DIPAH = Di-iso-propylamine;
[2]BC = benzyl chloride.

TABLE 6

Results for the Examples from Table 5

| Example | OH | Mg | Cl | Li | DIPAH | AB[1] | LiCl[2] | Ratio LiCl:AB | Yield[3] % AB[4] | % LiCl[5] | % TMPH[5] | Concentration Weight % |
|---|---|---|---|---|---|---|---|---|---|---|---|---|
| | mmol/g | | | | | | mmol/g | | | | | |
| 4 | 1.36 | 0.71 | 1.33 | 0.60 | 0.69 | 0.63 | 0.60 | 0.95 | 89.9% | 78.7% | 93.9% | 10.1 |

[1]AB = active base;
[2]over Li;
[3]isolated yield without wash solutions;
[4]relative to quantity of benzyl chloride BC;
[5]relative to quantity used.

The invention claimed is:

1. A process for forming an amidomagnesium halogenide of formula R'R"NMgX, the process comprising:

reacting, in an aprotic organic solvent or solvent mix, magnesium and an organic halide of formula $R^1X$ in the presence of a protic amine of formula R'R"NH and an alkali metal salt of formula MY to produce a mixture comprising an amidomagnesium halogenide of formula R'R"NMgX and an alkali metal salt of formula MY;

wherein:

the organic halide of formula $R^1X$ is selected from the group consisting of methyl chloride, methyl bromide, ethyl chloride, ethyl bromide, n-propyl chloride, iso-propyl chloride, n-propyl bromide, iso-propyl bromide, n-butyl chloride, sec-butyl chloride, tert-butyl chloride, n-butyl bromide, sec-butyl bromide, tert-butyl bromide, n-pentyl chloride, iso-pentyl chloride, sec-pentyl chloride, tert-pentyl chloride, n-pentyl bromide, iso-pentyl bromide, sec-pentyl bromide, tert-pentyl bromide, n-hexyl chloride, n-hexyl bromide, chlorobenzene, bromobenzene, benzyl chloride and benzyl bromide;

M is lithium, sodium or potassium,

Y is selected from the group consisting of chloride, bromide, iodide and OZ, wherein OZ represents an alcoholate anion and Z is selected from an organic, branched or unbranched, saturated or unsaturated aliphatic or aromatic carbon fragment which is between one and 20 carbon atoms or is selected from $R^2R^3R^4Si$, wherein $R^2$, $R^3$ and $R^4$ are independently selected from the group consisting of saturated, unsaturated, branched, unbranched, functionalized, unfunctionalized aliphatic, cyclic, heterocyclic or aromatic organic fragments of 1 to 20 carbon atoms; and the protic amine of formula R'R"NH is selected from the group consisting of dimethylamine, diethylamine, di-n-propylamine, di-iso-propylamine, di-n-butylamine, di-sec-butylamine, di-tert-butylamine, dicyclohexylamine, N-tertbutyl-iso-propylamine, hexamethyldisilazane, piperidine, and 2,2,6,6-tetramethylpiperidine, wherein the molar ratio of R'R"NH to R1X is between 0.7 to 1.5.

2. The process of claim 1, wherein the magnesium is in the form of chips, shavings, raspings, granules or a powder.

3. A process according to claim 1, wherein the magnesium is activated by addition of iodine, trimethylsilyl chloride, a previously prepared Grignard solution of formula $R^1MgX$ or a previously prepared product R'R"NMgX or admixtures thereof with an alkali metal salt.

4. A process according to claim 3, wherein the Grignard solution of formula $R^1MgX$ or previously prepared product R'R"NMgX and or admixtures thereof with an alkali salt is in an amount between 0.01 and 50 mol % relative to the magnesium.

5. A process according to claim 1, wherein the magnesium is in an excess of between 10 and 200% relative to the organic halide of formula $R^1X$.

6. A process according to claim 1, wherein the aprotic organic solvent is a mixture of ethers and hydrocarbons.

7. A process according to claim 1, wherein the organic halide of formula $R^1X$ forms volatile gases during the process.

8. A process according to claim 1, wherein the wherein $R^1$, $R^2$, $R^3$, $R^4$, R' and R" are independently selected from the group consisting of: methyl, n-propyl, iso-propyl, n-butyl, sec-butyl, tert-butyl, pentyl, hexyl, heptyl, octyl, cyclohexyl, phenyl, and benzyl.

9. A process according to claim 1, wherein the product R'R"NMgX has a concentration between 5 and 80 wt %.

10. A process according to claim 1, wherein M is lithium or potassium.

11. A process according to claim 10, wherein the alkali metal salt is selected from the group consisting of lithium chloride, lithium bromide, lithium methoxide, lithium ethoxide, lithium n-propoxide, lithium-iso-propoxide, lithium tert-butoxide, lithium tert-amoxide, lithium trimethysilyl oxide and lithium tri-tert-butylsilyl oxide.

12. A process according to claim 1, wherein an excess of 0-50% of alkali metal salt, based on the desired molar ratio of MY to R'R"NMgX, is provided.

13. A process according to claim 7, wherein an excess of 0-50% of alkali metal salt, based on the desired molar ratio of MY to R'R"NMgX, is provided.

14. A process according to claim 1, wherein:

the organic halide is metered into the aprotic organic solvent or solvent mix after the magnesium and the protic amine are placed in the aprotic organic solvent or solvent mix; or the protic amine and the organic halide are metered into the aprotic organic solvent or solvent mix either as a mixture or individually in parallel, after the magnesium is placed in the aprotic organic solvent or solvent mix.

15. A process according to claim 1, wherein the process comprises reacting, in the aprotic organic solvent or solvent mix, ingredients consisting of magnesium, the organic halide, the protic amine, and the alkali metal salt.

* * * * *